United States Patent [19]

Suzuki et al.

[11] 4,398,040

[45] Aug. 9, 1983

[54] PROCESS FOR PRODUCING TRIMELLITIC ACID

[75] Inventors: Takashi Suzuki; Koichi Kitahara; Susumu Naito; Tomoji Tsuji, all of Niigata, Japan

[73] Assignee: Mitsubishi Gas Chemical Company, Inc., Tokyo, Japan

[21] Appl. No.: 388,234

[22] Filed: Jun. 14, 1982

Related U.S. Application Data

[63] Continuation of Ser. No. 210,860, Nov. 26, 1980, abandoned.

[30] Foreign Application Priority Data

Nov. 28, 1979 [JP] Japan ............................. 54-153814

[51] Int. Cl.$^3$ .............................................. C07C 51/16
[52] U.S. Cl. ................................................... 562/413
[58] Field of Search ............................... 562/413, 416

[56] References Cited

U.S. PATENT DOCUMENTS 3,683,016 8/1972 Darin et al. ......................... 562/413
3,920,735 11/1975 Wampfler et al. .................. 562/416

Primary Examiner—Alan Siegel
Attorney, Agent, or Firm—Armstrong, Nikaido, Marmelstein & Kubovcik

[57] ABSTRACT

Trimellitic acid is produced in higher yield by liquid phase air oxidation of pseudocumene in acetic acid as a solvent in the presence of cobalt, manganese, and bromine as a catalyst, where the oxidation is carried out at two stages comprising a first stage of reaction at a temperature of 110° to 170° C. and a second stage of reaction at a temperature of 180° to 240° C. while maintaining a reaction pressure under a condition of the following formula throughout the reaction:

$$1.20\ P_{solv} \leq P \leq 2.20\ P_{solv}$$

wherein P represents a reaction pressure as absolute pressure and Psolv represents a total vapor pressure of acetic acid and water present in a reaction system at a given reaction temperature.

14 Claims, No Drawings

PROCESS FOR PRODUCING TRIMELLITIC ACID

This is a continuation of application Ser. No. 210,860, filed Nov. 26, 1980, now abandoned.

This invention relates to a process for producing trimellitic acid, and more particularly to a process for producing trimellitic acid in high yield by liquid phase air oxidation of pseudocumene in acetic acid in the presence of cobalt, manganese and bromine as a catalyst through selection of specific reaction temperature and pressure.

Trimellitic acid is an aromatic tribasic acid, which is important as a raw material for a high grade plasticizer or heat-resistant plastics.

Pseudocumene as a raw material for trimellitic acid is obtained as a $C_9$ fraction in catalytically reformed oil or thermally cracked oil residue, and can be readily obtained as a high purity product only by distillation because of its relatively large difference in boiling point from other components.

Nitric acid oxidation and air oxidation are known for oxidation of pseudocumene to trimellitic acid. The nitric acid oxidation is expensive in oxidizing agent cost and produces nitro compounds, etc. as by-products, whereas the air oxidation requires a high pressure as a reaction condition, but is more advantageous.

Air oxidation of pseudocumene is carried out in the presence of a heavy metal catalyst in the same manner as in the case of air oxidation of alkylaromatic compounds such as p-xylene or m-xylene. However, in the case of air oxidation of pseudocumene, the product trimellitic acid has two carboxyl groups at the ortho positions, and thus forms complexes with the heavy metal of the catalyst, lowering the catalyst activity. Thus, the oxidation yield is generally regarded as lower than that of air oxidation of other alkylaromatic compounds having no such structure.

Under these situations, various attempts have been made to improve the catalyst system for air oxidation of pseudocumene. For example, a process of successively adding catalyst components of cobalt, manganese, cerium and bromine (Japanese Laid-open Patent Application Specification No. 7173/71), and a process of adding zirconium to cobalt, manganese and bromine (Japanese Laid-open Patent Application Specification No. 18434/75) were proposed. The oxidation yield could be increased by these improvements about catalyst, but the catalyst systems were so complicated that it was difficult to recover and reuse the catalysts. This has been a new problem.

Liquid phase air oxidation of alkylaromatic compounds requires mass transfer between gas and liquid, generates a large amount of heat, and produces a slurry of insoluble product, and thus a tank reactor of complete mixing type has been widely utilized commercially.

Even in the production of trimellitic acid it also seemed suitable to use the tank reactor of complete mixing type, but it was found that the oxidation of pseudocumene gaves rise to lots of side reactions, and trimellitic acid yield was extremely lowered in a continuous operation in the tank reactor of complete mixing type as used in the oxidation of p-xylene.

The present inventors proposed a process for continuously producing trimellitic acid in a tank reactor of complete mixing type by using two stages of reaction temperature at a controlled catalyst concentration of a simple catalyst system, where the catalyst could be readily recovered and reused, and a high trimellitic acid yield could be obtained in a continuous stable operation.

However, in the proposed process, the first stage of reaction temperature was 110°–170° C., and special caution was required for removing the heat of reaction. For example, in the production of terephthalic acid similar to trimellitic acid, it was possible to remove the heat of reaction through evaporation in the reaction system when the reaction was carried out at a reaction temperature of 180° C. or higher, whereas it was impossible to remove the heat of reaction through such latent heat of evaporation when the reaction was carried out at a reaction temperature of 150° C. or lower, and the removal of heat had to be made through the heat transfer surface of a heat exchanger. Such relationship between the reaction temperature and the way to remove the heat of reaction similarly applies to the production of trimellitic acid. That is, in the air oxidation in a low temperature range of 150° C. or lower, evaporation was impossible under an oxygen partial pressure of 1 atm or higher, that is, under a total pressure of 5 atm or higher as disclosed in Japanese Patent Publication No. 39663/74, and a difficulty in cooling trimellitic acid having a relatively high solubility in a solvent through a heat transfer surface has been a problem in commercial application.

To overcome such a problem, the present inventors have made extensive study of reaction conditions, and, as a result, have found that the reaction proceeds smoothly under a very low oxygen partial pressure in the oxidation of pseudocumene to trimellitic acid, using plural stages of reaction temperature, and have established the present invention on the basis of the finding.

The present invention provides a process for producing trimellitic acid by liquid phase air oxidation of pseudocumene in acetic acid in the presence of cobalt, manganese and bromine as a catalyst, which comprises conducting the reaction at two stages comprising a first stage of reaction at a temperature of 110° to 170° C. and a second stage of reaction at a temperature of 180° to 240° C., while maintaining a reaction pressure under a condition of the following formula throughout the reaction:

$$1.20 P_{solv} \leq P \leq 2.20 P_{solv}$$

wherein P represents a reaction pressure (absolute) and $P_{solv}$ represents a total vapor pressure of acetic acid and water present in a reaction system at a given reaction temperature.

The catalyst used in the present invention is a combination system of two kinds of heavy metals, cobalt and manganese, with bromine. Other heavy metal than cobalt and manganese can be used, but is not advantageous from the viewpoint of catalyst amount. The amount of cobalt and manganese to be used must be 0.05 to 0.5% by weight in terms of total atomic concentration on the basis of total amount of acetic acid and water present in the reaction system at the start of reaction. Below 0.05% by weight, smooth progress of reaction is interrupted, and oxidation fails to proceed stationarily, or the trimellitic acid yield is sometimes greatly lowered.

Above 0.5% by weight, on the other hand, no improvement can be obtained at all from the viewpoint of reaction, or rather combustion reaction of acetic acid is disadvantageously increased.

Atomic ratio of cobalt to manganese is most preferably 1:1, but there is no great trouble at all even in the atomic ratio of 1:4–4:1.

Atomic ratio of bromine to total amount of cobalt and manganese is in a range of 1.5–2.5, and most preferably 2.0.

It is possible to change the composition of the catalyst between the first stage of reaction at a lower temperature and the second stage of reaction at a higher temperature. However, it is particularly preferable not to change the composition of the catalyst when the catalyst is recovered by dehydrating and purifying the mother liquor freed from trimellitic acid, thereby concentrating the catalyst components and recycling them to the oxidation step.

Cobalt and manganese can be used in the form of organic acid salts such as acetate, propionate, butyrate, etc., inorganic salts such as halides, sulfates, etc., or organic complexes.

Bromine can be used in the form of not only simple bromine, but also inorganic bromides, hydrobromic acid and organic bromides.

Cobalt bromide, manganese bromide, etc. can be used as compounds containing two species of catalyst components.

The solvent to be used in the present invention is acetic acid, and other aliphatic carboxylic acids than acetic acid can be used, but are not practical.

Acetic acid is not required to be anhydrous, and in view of the load in the acetic acid purification step, commercially advantageously applicable acetic acid is 95% by weight acetic acid (water content: 5% by weight).

The amount of solvent acetic acid to be used is preferably 1.0 to 5.0 parts by weight per part by weight of raw material pseudocumene at the initial charging at the first stage of reaction at the lower temperature, but 2.0 to 3.0 parts by weight of acetic acid is particularly preferable for increasing a space-time-yield (STY) in a reactor.

Outside the above-mentioned range of acetic acid, stationary reaction fails to proceed, or the product cannot be obtained in a good yield.

In the present invention, oxidation reaction temperature is 110° to 170° C. at the first stage of reaction, that is, the first stage of lower reaction temperature, and 180° to 240° C. at the second stage of reaction, that is, the second stage of higher reaction temperature, and preferably 120° to 150° C., and 195° to 225° C., respectively.

Outside the above-mentioned ranges of reaction temperature, production of by-products is increased, lowering the trimellitic acid yield.

The present invention can be carried out batch-wise, semi-continuously or continuously. The first stage of reaction can be carried out batch-wise, whereas the second stage of reaction can be carried out continuously.

In the case of batch-wise operation throughout the first and second stages of reaction, the present invention can be carried out in one and same reactor by setting the lower reaction temperature and then the higher reaction temperature with time. According to a particularly preferable mode of embodiment, the reaction is started at 110° to 130° C., and temperature is gradually or rapidly elevated to 220° to 240° C. as the reaction proceeds, and then the reaction is completed at 220° to 240° C.

According to the above-mentioned mode of embodiment, the reaction temperature can be controlled by adjusting a reaction pressure. That is, after the reaction has been started at 110° to 130° C., the temperature can be elevated to the ultimate reaction temperature of 220° to 240° C. only by the heat of reaction without using any heat exchanger for temperature elevation. This is a commercially advantageous mode.

In the foregoing batch-wise case, the reaction inevitably passes through the intermediate temperature range from the temperature range at the first stage of reaction to that at the second stage of reaction, but this is no problem at all.

In the case of carrying out the present invention continuously throughout the first and second stages of reaction, it is preferable to use a reactor comprised of at least one tank of complete mixing type kept in the lower temperature range at the first stage of reaction and at least one tank of complete mixing type kept in the higher temperature range at the second stage of reaction, the individual tanks being connected to one another in series.

In the case of carrying out the present invention by conducting the first stage of reaction batch-wise and the second stage of reaction continuously, the batch-wise operation at the first stage of reaction is carried out in the lower temperature range by keeping the temperature in that temperature range only by the heat of reaction, and then the reaction solution is continuously supplied to a tank of complete mixing type kept in the higher temperature range, while withdrawing the product solution therefrom.

The main factor for selecting the reaction time for the first stage of reaction at the lower reaction temperature (in the case of continuous operation, residence time, that is, amount of resident solution in tank/solution flow rate, which will be hereinafter referred to as "reaction time", unless otherwise mentioned) is the amount of unreacted pseudocumene in the reaction solution. That is, it is necessary to proceed with the reaction at the first stage of reaction at the lower reaction temperature until the amount of unreacted pseudocumene in the reaction solution becomes 10% or less on the basis of charged pseudocumene. If the reaction solution containing more than 10% of unreacted pseudocumene on the basis of charged pseudocumene is supplied to the second stage of reaction at the higher reaction temperature, and subjected to further oxidation reaction, the trimellitic acid yield will never exceed 80%.

In the oxidation to 10% or less of unreacted pseudocumene on the basis of charged pseudocumene, usually 1.5 to 2.0 moles of oxygen is absorbed per mole of charged pseudocumene.

The reaction time for the first stage of reaction depends upon the preset conditions, but is usually in a range of 30 minutes to 3 hours.

On the other hand, the reaction time for the second stage of reaction at the higher reaction temperature is set so that total residual amount of dimethylbenzoic acid and methylphthalic acid in the reaction solution may be less than 10% by mole on the basis of charged pseudocumene. If the residual amount of these oxidation intermediates is larger, the load will be increased in the successive purification step.

At the second stage of reaction, it is preferable to complete the reaction when there is no substantial absorption of oxygen. The reaction time depends upon the preset conditions, but is usually in a range of 30 minutes to 3 hours.

In the present invention, an applicable range of reaction pressure is determined on the basis of total vapor pressure of acetic acid and water at a given reaction temperature and is an important factor for removing the heat of reaction by evaporation.

The acetic acid used herein is the solvent, whereas the water includes the one supplied to the reaction system as contained in the acetic acid and the one formed by the reaction. Combustion reaction of acetic acid also takes place, and proportion of acetic acid to water is usually changeable with the progress of oxidation. For example, there are 85 to 80% by weight of acetic acid and 15 to 20% by weight of water under a typical condition.

In the present invention, reaction pressure P must satisfy the following formula, where Psolv represents total vapor pressure of acetic acid and water without taking any influence of solute into account.

$$1.20\overline{P}solv \leq P \leq 2.20\overline{P}solv$$

According to the present invention, oxidation reaction is carried out by injecting air as an oxygen source into the reaction system, and discharging the effluent gas as it is, but the amount of air to be injected is adjusted so that the oxygen concentration of the effluent gas may be less than 8% by volume to avoid the operation within the explosion limits, as in the ordinary commercial operation.

So long as the amount of air to be injected is adjusted in the above-mentioned manner, the heat of reaction and the heat of evaporation are balanced against each other under the reaction pressure satisfying the above-mentioned formula, and the reaction can be smoothly carried out without using any special temperature control means. On the other hand, in the case of $P < 1.20 \cdot \overline{P}solv$, the heat is too much removed by air injection to maintain the reaction temperature, and consequently the reaction temperature is lowered and the reaction conditions cannot be maintained as such. In the case of $2.20\overline{P}solv < P$, evaporating vapors are too little to remove the heat of oxidation reaction only by the latent heat of evaporation, and consequently the reaction temperature is increased.

According to the present invention, the oxidation reaction can be smoothly carried out without using any special temperature controlling means, and trimellitic acid can be produced in high yield while suppressing the side reactions.

The present invention will be described in detail below, referring to the Comparative Example and Examples, where atmosphere (atm) is an obsolute pressure.

COMPARATIVE EXAMPLE

Reaction was carried in a titanium reactor, 80 mm in inner diameter and 2 l in net capacity, provided with a reflux condenser, a reaction solution charge nozzle, an air injection nozzle, and a nozzle for discharging the content.

The reactor was further provided with a rotating stirrer with four turbine blades and a heating-cooling jacket.

Into the reactor were charged 350 g of pseudocumene, 900 g of acetic acid, 47 g of water, 1.60 g of cobalt acetate, 1.69 g of manganese acetate, and 2.16 g of hydrogen bromide, and reaction was carried out by injecting air under a pressure of 22.3 atm. Reaction temperature was kept at 130° C. until 1.5 moles of oxygen had been absorbed per mole of charged pseudocumene, while the heat of oxidation reaction was removed by forced heat exchange through the reactor jacket. After 1.7 moles of oxygen had been absorbed per mole of charged presudocumene (residual amount of pseudocumene: 10% on the basis of charged pseudocumene), reaction temperature was elevated from 130° C. to 220° C., while keeping the reaction pressure at 22.3 atm, and the reaction temperature was kept at 220° C.

At the reaction temperature of 220° C., the heat of oxidation reaction was removed by refluxing of condensate, while effecting heating through the reactor jacket to prevent heat radiation from the surface of the reaction. The same operation was conducted in Examples which follow.

Air injection was continued at 220° C. until there was no substantial oxygen absorption, and then the reactor was cooled, and the reaction product was discharged from the reactor, and analyzed.

It was found that trimellitic acid yield on the basis of charged pseudocumene was 79.2% by mole, and by-produced methylphthalic acid was 1.8% by mole.

Relationship between Psolv and P in the course of reaction in the present Comparative Example is given in Table 1.

TABLE 1

| | Temp. °C. | Pressure P atm. | Water concentration wt. % | Psolv atm. | P/Psolv |
|---|---|---|---|---|---|
| At start of first stage of reaction | 130 | 22.3 | 5 | 1.7 | 13.1 |
| At end of the first stage of reaction | " | " | 7.4 | 1.8 | 12.4 |
| At start of second stage of reaction | 220 | " | 7.4 | 14.9 | 1.5 |
| At end of second stage of reaction | " | " | 17.0 | 17.0 | 1.3 |

EXAMPLE 1

Reaction was carried out with the same raw materials in the same reactor as used in Comparative Example.

Oxidation reaction was carried out by elevating reaction temperature from 120° C. to 220° C. continuously at a temperature elevation rate of 40° C./hr, while changing reaction pressure from 2.5 atm at the start of air injection to 22.3 atm.

Relationship among reaction temperature, P, and Psolv are given in Table 2.

TABLE 2

| Temp. °C. | Pressure P atm. | Water concentration wt. % | Psolv atm. | P/Psolv | Oxygen absorbed mol/Pseudocumene mol |
|---|---|---|---|---|---|
| 120 | 2.5 | 5.0 | 1.3 | 1.9 | 0 |
| 140 | 3.9 | 6.3 | 2.4 | 1.6 | 0.8 |
| 160 | 6.8 | 7.9 | 4.3 | 1.6 | 1.8 |
| 180 | 10.7 | 9.6 | 7.2 | 1.5 | 2.8 |
| 200 | 15.5 | 11.2 | 11.2 | 1.4 | 3.8 |
| 220 | 22.3 | 12.3 | 16.0 | 1.4 | 4.5 |

At 160° C. and 1.8 moles of oxygen absorbed/mole of pseudocumene, the residual pseudocumene amounted to 10% on the basis of charged pseudocumene. At 170° C., the amount of oxygen absorbed was 2.2 moles/mole of pseudocumene.

After the injection of air had been continued at 220° C. until there was no substantial oxygen absorption, the reactor was cooled, and the reaction product was withdrawn and analyzed. Refluxing from the reflux condenser was observed throughout the entire period of reaction with the injection of air.

Trimellitic acid yield on the basis of the charged pseudocumene was 81.4% by mole, and the by-product methylphthalic acid yield was 0.8% by mole, which were substantially equal to the yields in the two-stage reaction at lower and higher temperature under a higher pressure in Comparative Example.

EXAMPLE 2

Reaction was carried out with the same raw materials in the same reactor as used in Comparative Example.

The reaction was carried out by starting injection of air at 130° C. under a pressure of 3.4 atm and continued at the same temperature under the same pressure until the oxygen absorption by reaction amounted to 1.2 moles/mole of pseudocumene, and then temperature and pressure were elevated to 220° C. and 22.3 atm, respectively, in the same manner as in Example 1 to complete the oxidation reaction. The temperature elevation rate was 90° C./hr at that time, the pressure was set to the respective temperatures at the temperature elevation operation in the same manner as in Example 1.

The oxygen absorption amounted to 1.7 moles/mole of pseudocumene at 160° C., and the residual pseudocumene amounted to 10% on the basis of charged pseudocumene. The oxygen absorption at 170° C. amounted to 2.1 mole/mole of pseudocumene.

The result of reaction was that trimellitic acid yield on the basis of the charged pseudocumene was 81.9% by mole, and 1.2% by mole of methylphthalic acid was by-produced.

EXAMPLE 3

Reaction was carried out with the same raw materials in the same reactor as used in Comparative Example, where injection of air was started at 130° C. under a pressure of 3.4 atm in the same manner as in Example 2, and after 1.1 mole of oxygen had been absorbed per mole of pseudocumene, temperature and pressure were rapidly elevated to 220° C. and 22.3 atm, respectively, to conduct reaction substantially at two stages of temperature and two stages of pressure. It took 15 minutes to elevate the temperature from 130° C. to 220° C. After the injection of air had been continued at 220° C. until there was no substantial oxygen absorption, the reactor was cooled, and the reaction product was withdrawn from the reactor and analyzed.

The oxygen absorption amounted to 1.8 moles per mole of pseudocumene at 160° C., and the residual pseudocumene amounted to 10% on the basis of charged pseudocumene. The oxygen absorption at 170° C. amounted to 2.2 moles per mole of pseudocumene.

The result of reaction was that the trimellitic acid yield on the basis of the charged pseudocumene was 81.9% by mole, and 2.0% by mole of methylphthalic acid was by-produced.

Relationship between P and $\bar{P}solv$ in the course of reaction is given in Table 3.

TABLE 3

| | Reaction temp. °C. | Water concentration % | $\bar{P}solv$ atm. | P atm. | P/$\bar{P}solv$ atm. |
|---|---|---|---|---|---|
| At start of first stage of reaction | 130 | 5.0 | 1.7 | 3.4 | 2.0 |
| At end of first stage of reaction | " | 6.8 | 1.7 | " | 2.0 |
| At start of second stage of reaction | 220 | " | 14.6 | 22.3 | 1.5 |
| At end of second stage of reaction | " | 12.3 | 16.0 | " | 1.4 |

EXAMPLE 4

Reaction was continuously carried out by one pass flow with raw materials as shown in Table 4 in two units of the same reactors connected to each other in series as in Comparative Example.

The raw materials were charged into the reactor at the first stage of reaction, and reaction was started at 130° C. under a pressure of 3.9 atm. While supplying the raw materials into the reactor at the first stage at a preset flow rate, the reaction solution was withdrawn from the reactor so that the liquid level could be kept constant in the reactor, and supplied into the reactor at the second stage, which was kept at 220° C. under a pressure of 22.3 atm.

The water concentration, $\bar{P}solv$ and P/$\bar{P}solv$ were 9.2%, 2.0 atm and 1.9, respectively, at the first stage of reaction and 14.0%, 17.0 atm, and 1.3, respectively, at the second stage of reaction.

After the composition of reaction solution had been brought into a stationary state at the second stage of reaction, the reaction solution was sampled and analyzed. The result of reaction is given in Table 4.

TABLE 4

| Charging flow rate | Pseudocumene | g/Hr | 192 |
|---|---|---|---|
| | Acetic acid | " | 493 |
| | Water | " | 29 |
| | Cobalt acetate | " | 3.30 |
| | Manganese acetate | " | 3.48 |
| | Hydrogen bromide | " | 4.44 |
| First stage of reaction | Temperature | °C. | 130 |
| | Pressure | atm | 3.9 |
| | Effluent gas flow rate | Nl/Hr | 480 |
| | Residence time | Hr | 2.3 |
| | Oxygen absorption | mol/mol | 2.5 |
| First stage yield | Pseudocumene | % | 3.5 |
| | Dimethylbenzoic acid | % | 28.3 |
| | Methylphthalic acid | % | 44.3 |
| | Trimellitic acid | % | 12.8 |
| Second stage of reaction | Temperature | °C. | 220 |
| | Pressure | atm | 22.3 |
| | Effluent gas flow rate | Nl/Hr | 430 |
| | Residence time | Hr | 1.8 |
| | Oxygen absorption | mol | 2.8 |
| Ultimate yield | Pseudocumene | % | — |
| | Dimethylbenzoic acid | % | 0.3 |
| | Methylphthalic acid | % | 3.4 |
| | Trimellitic acid | % | 76.0 |

What is claimed is:

1. A process for producing trimellitic acid by liquid phase air oxidation of pseudocumene in an acetic acid reaction medium in the presence of a catalyst consisting of of catalytic forms of cobalt, manganese and bromine, which comprises conducting the reaction at two stages comprising a first stage of reaction at a temperature of 110° to 170° C. and a second stage of reaction at a temperature of 180° to 240° C., while maintaining a reaction pressure under a condition of the following formula throughout the reaction:

$$1.20\overline{P}solv \leq P \leq 2.20\overline{P}solv$$

wherein P represents a reaction pressure as absolute pressure and $\overline{P}solv$ represents a total vapor pressure of acetic acid and water present in the reaction system at a given reaction temperature and the first stage of reaction at a lower temperature is continued until the amount of unreacted pseudocumene in the reaction solution becomes 10% or less on the basis of charged pseudocumene.

2. A process according to claim 1, wherein the cobalt and the manganese are used at total atomic concentration of 0.05 to 0.5% by weight on the basis of total of acetic acid and water present at the start of reaction.

3. A process according to claim 1, wherein an atomic ratio of the cobalt to the manganese is 1:4–4:1.

4. A process according to claim 1, wherein an atomic ratio of bromine to total of the cobalt and the manganese is 1.5–2.5:1.

5. A process according to claim 1, wherein 1.0 to 5.0 parts by weight of the acetic acid is used per part by weight of the pseudocumene at the initial charging at the first stage of reaction.

6. A process according to claim 1, wherein the first stage of reaction is carried out at 120° to 150° C. and the second stage of reaction is carried out at 195° to 225° C.

7. A process according to claim 1, wherein the reaction is carried out batchwise, semi-continuously or continuously.

8. A process according to claim 1, wherein the first stage of reaction is carried out batchwise, and the second stage of reaction is carried out continuously.

9. A process according to claim 8, wherein the first stage of batch-wise reaction is carried out at the lower temperature by keeping the temperature only by the heat of reaction, and then the reaction solution is continuously supplied to a tank of complete mixing type kept at the higher temperature at the second stage of continuous reaction, and product solution is continuously withdrawn from the tank.

10. A process according to claim 1, wherein the first stage and second stages of reaction are carried out batchwise.

11. A process according to claim 10, wherein the first stage of batch-wise reaction is started at 110° to 130° C., and the second stage of batchwise reaction is completed by elevating the reaction temperature to 220° to 240° C. in one and same reactor.

12. A process according to claim 11, wherein the first stage of batch-wise reaction is started at 110° to 130° C. and the second stage of batch-wise reaction is completed by elevating the temperature to 220° to 240° C. only by the heat of reaction by controlling a reaction pressure.

13. A process according to claim 1, wherein the second stage of reaction is continued until the total residual amount of dimethylbenzoic acid and methylphthalic acid in reaction solution becomes less than 10% by mole.

14. A process according to claim 1, wherein the air is injected into reaction system, so that the oxygen concentration of effluent gas from the reaction system is less than 8% by volume.

* * * * *